United States Patent
Dai et al.

(10) Patent No.: US 9,428,441 B2
(45) Date of Patent: Aug. 30, 2016

(54) METHOD FOR REMOVING HCN FROM CRUDE DINITRO TOLUENE

(71) Applicant: BASF SE, Ludwigshafen (DE)

(72) Inventors: Yuan Shen Dai, Shanghai (CN); Katharina Spuhl, Ludwigshafen am Rhein (DE); Renate Hempel, Ruhland (DE)

(73) Assignee: BASF SE (DE)

( * ) Notice: Subject to any disclaimer, the term of this patent is extended or adjusted under 35 U.S.C. 154(b) by 0 days.

(21) Appl. No.: 14/916,210

(22) PCT Filed: Sep. 1, 2014

(86) PCT No.: PCT/EP2014/068464
§ 371 (c)(1),
(2) Date: Mar. 3, 2016

(87) PCT Pub. No.: WO2015/032706
PCT Pub. Date: Mar. 12, 2015

(65) Prior Publication Data
US 2016/0194270 A1     Jul. 7, 2016

(30) Foreign Application Priority Data
Sep. 5, 2013  (EP) .................................. 13183198

(51) Int. Cl.
*C07C 205/00* (2006.01)
*C07C 201/16* (2006.01)
*C07C 201/08* (2006.01)
*C07C 205/06* (2006.01)

(52) U.S. Cl.
CPC ........... *C07C 201/16* (2013.01); *C07C 201/08* (2013.01); *C07C 205/06* (2013.01)

(58) Field of Classification Search
CPC .. C07C 201/08; C07C 201/16; C07C 205/06

USPC ......................................................... 568/934
See application file for complete search history.

(56) References Cited

U.S. PATENT DOCUMENTS

| 5,001,286 | A | 3/1991 | Witt et al. |
| 5,756,867 | A | 5/1998 | Hermann et al. |
| 6,191,325 | B1 | 2/2001 | Marion et al. |
| 7,470,826 | B2 | 12/2008 | Hermann et al. |

FOREIGN PATENT DOCUMENTS

| EP | 0040429 A1 | 11/1981 |
| EP | 0 279 312 A2 | 8/1988 |
| EP | 0736514 A1 | 10/1996 |
| EP | 0897907 A1 | 2/1999 |
| EP | 1780195 A1 | 5/2007 |

OTHER PUBLICATIONS

International Search Report for PCT/EP2014/068464 mailed Nov. 3, 2014.
Quakenbush, A., et al., "The Olin Dinitrotoluene (DNT) Process", Polyurethanes World Congress 1993, Technomic Publishing Co., pp. 484-488.

*Primary Examiner* — Jafar Parsa
(74) *Attorney, Agent, or Firm* — Drinker Biddle & Reath LLP

(57) ABSTRACT

A process for the preparation of dintrotoluene which comprises (a) nitrating toluene with a nitrating acid, wherein said nitrating acid is a mixture of nitric acid and sulfuric acid, in one or more nitration steps, and separating the nitrating acid from the process stream thus formed, wherein a crude mixture comprising dinitrotoluene and a fraction of said nitrating acid dissolved therein is obtained, said crude mixture further comprising at least 50 ppm of HCN, and (b) washing the crude dinitrotoluene containing mixture in one or more washing steps, wherein, before the first washing step is carried out, the crude mixture is distilled and/or stripped to remove HCN therefrom, wherein a crude dinitrotoluene containing mixture which is essentially free of HCN is obtained.

11 Claims, No Drawings

METHOD FOR REMOVING HCN FROM CRUDE DINITRO TOLUENE

CROSS-REFERENCE TO RELATED APPLICATIONS

This application is a national stage application (under 35 U.S.C. §371) of PCT/EP2014/068464, filed Sep. 1, 2014, which claims benefit of European Application No. 13183198.4, filed Sep. 5, 2013, both of which are incorporated herein by reference in their entirety.

The invention concerns a process for the preparation of dinitrotoluene.

Aromatic nitro compounds like dinitrotoluene (DNT) or mononitrobenzene (MNB) are commercially produced through nitration of an aromatic with a mixture of nitric acid and sulfuric acid. The reaction is a biphasic reaction, typically the reaction rate is determined by the mass transfer between the two phases. In case of toluene nitration the reaction is typically carried out isothermally, toluene is present in molar substochiometry which means the molar ration of nitric acid to toluene is >1, typically 1.01-1.2. In a first step the toluene is nitrated to form mononitrotoluene (MNT). The biphasic reaction mixture undergoes phase separation into an aqueous phase containing the main part of sulfuric acid and an organic phase containing the main part of MNT. The organic phase then undergoes nitration to DNT in a further biphasic reaction. Again the reaction mixture undergoes phase separation into an aqueous phase and an organic phase containing DNT.

During the nitration reaction different undesired side reactions take place, like the formation of picric acid, cresols or nitrocresols. One of the most hazardous side products is however HCN.

In the continuous isothermal or adiabatic nitration of toluene to form DNT, a crude nitroaromatic product is always obtained after phase separation and this has to be freed of the impurities dissolved therein before further use. Apart from the final nitrating acid composed of nitric acid, sulfuric acid and nitrogen oxides which is present in dissolved form or as microemulsion in the nitroaromatic, oxidation products from secondary reactions with the aromatic to be nitrated, e.g. mononitrocresols, dinitrocresols and trinitrocresols, or aromatic carboxylic acids, e.g. mononitrobenzoic and dinitrobenzoic acids and degradation products thereof, are also comprised in the crude DNT.

In the prior art, these impurities are removed from the crude product by means of a multistage scrub before the nitroaromatic is passed to a direct use, an isomer separation or a hydrogenation to form the corresponding amines.

The scrub to which the crude nitroaromatic such as DNT is subjected to remove the therein-dissolved and -suspended acids of the nitration mixture, the nitrocresols and other acidic and further impurities which can be extracted by means of the scrubbing medium usually comprises three steps:

1. a scrub to remove the dissolved and suspended mineral acids such as sulfuric acid, nitric acid and nitrogen oxides (acid scrub);
2. a scrub in the presence of a base (alkali scrub) such as sodium carbonate (soda), sodium bicarbonate, ammonia, sodium hydroxide, potassium hydroxide, etc. to remove the weakly acidic impurities dissolved in the crude nitroaromatic, e.g. nitrocresols, nitrobenzoic acids and degradation products from the oxidative degradation of the nitrocresols or of aliphatic or cyclic hydrocarbons, e.g. oxalic acid;
3. a neutral scrub to remove residual traces of alkali and further reduce the impurities remaining in traces in the product. Water is usually used as scrubbing medium for this purpose and the scrub is carried out as a liquid/liquid scrub at the temperatures at which the nitroaromatic to be scrubbed is present as a liquid.

The objective of these scrubs is to obtain not only a pure product but as little as possible wastewater per metric ton of product and to achieve a level of scrubbed-out impurities in the wastewater which enables disposal of said impurities to be carried out inexpensively.

To minimize the amount of water required for this scrub, the scrub is carried out in countercurrent, with the water used for the neutral scrub being employed, after addition of bases, in the alkali scrub (see A. B. Quakenbush et. al., The Olin Dinitrotoluene (DNT) Process, Polyurethane World Congr. Proc. 1993, Publish.: Technomic Lancaster, p. 485) or with the acid scrub being carried out using a minimum amount of water so as to give a concentrated acid which, as described in EP 0 279 312, EP 0 736 514 and EP 1 780 195, can be recirculated directly or after further concentration to the nitration. The vapor condensates obtained in the concentration of scrubbing water are recirculated to the respective scrubs.

Before the wastewater from a plant for the nitration of toluene to form DNT, the scrubbing water from the scrubbing of the crude DNT and the vapor condensates from concentration of the final acids and scrubbing acids can be discharged, they have to be subjected to a complicated treatment in order to achieve the applicable discharge parameters as set down in the wastewater regulations for, for example, COD, nitrogen, heavy metals and biological parameters before introduction into an outfall drain.

Wastewater streams requiring treatment from nitration plants are the vapor condensate from concentration of the final nitrating acid (referred to as SAC wastewater), which is always acidic, and especially the wastewater from scrubbing with bases, which has a pH in the range 7-10. Before discharge into an outfall drain, all toxic, gene toxic or bacteriostatic substances have to be removed as far as possible from these wastewater streams in order for the discharge parameters laid down to be met.

The wastewater from the scrubbing of the DNT with bases comprises the dissolved product in an amount of up to 0.5%, corresponding to its solubility, together with the phenolic nitro compounds, nitrobenzoic acids and other organic acids and low molecular weight degradation products dissolved in the crude product. Apart from purely mechanical separation of the nitrocresols from the wastewater of a DNT scrub by means of bases, preferably sodium carbonate or sodium hydroxide, processes for treatment with activated carbon or ion exchange resins, processes of extraction with the aromatic to be nitrated, treatment with oxidants such as ozone or Fenton's reagent or treatment at high temperatures up to 300° C. have been described, in order to remove or decrease the amount of not only the nitro molecules, predominantly the product, but especially the phenolic nitro molecules such as dinitrophenols and trinitrophenols (picric acid) and dinitrocresols and trinitrocresols (TNCs) from/in the wastewater before this wastewater is passed to subsequent after-treatment in a water treatment plant.

Currently the HCN/CN⁻-specifications for waste streams are getting stricter, especially in China. The regulations for wastewater streams often stipulate HCN/CN⁻ concentrations of below 10 ppm, sometimes below 1 ppm, and some regions require levels below 0.3 ppm (e. g. Shanghai, China). Therefore HCN containing waste streams must be treated to reach the required low HCN/CN— concentrations. This is typically done for cyanide containing aqueous streams by addition of $H_2O_2$ or other oxidizing agents, or by treating the wastewater in an acidic unit like Fenton's reactor or by ozonolysis. In case of large wastewater streams, large amounts of oxidizing chemicals are necessary, which entails high costs for chemicals. Moreover, the DNT is typically sent to a hydrogenation reactor where toluylenediamine (TDA) is produced from the DNT. However, with cyanide/HCN present on the DNT there is a risk that the cyanide may be harmful to the DNT hydrogenation catalyst. Therefore not only removal of $HCN/CN^-$ from waste water streams but also from the DNT product streams is desirable.

It is an object of the present invention to provide a process for the preparation of dinitrotoluene by nitration of toluene wherein HCN is removed in a simple and efficient manner from the process streams, thereby avoiding the need of cumbersome wastewater aftertreatment procedures.

The object is achieved by a process for the preparation of dintrotoluene which comprises (a) nitrating toluene with a nitrating acid, wherein said nitrating acid is a mixture of nitric acid and sulfuric acid, in one or more nitration steps, and separating the nitrating acid from the process stream thus formed, wherein a crude mixture comprising dinitrotoluene and a fraction of said nitrating acid dissolved therein is obtained, said crude mixture further comprising at least 50 ppm of HCN, and (b) washing the crude dinitrotoluene containing mixture in one or more washing steps, wherein, before the first washing step is carried out, the crude mixture is distilled and/or stripped to remove HCN therefrom, wherein a crude dinitrotoluene containing mixture which is essentially free of HCN is obtained.

HCN that is contained in the crude DNT containing mixture is thus stripped out of the organic DNT phase before the crude mixture is passed from the reaction section through the washing section. Without removal of HCN before the washing section, HCN is dissolved both in the organic DNT phase and in the aqueous wash water phase in the first washing step and, being distributed among different phases, much more difficult to remove, since treatment of more than one process stream would be necessary. HCN, which is volatile, can be easily stripped out of either the organic phase or the aqueous phase. However, once HCN has been reacted with an alkaline media, e.g. in an alkaline washing step, HCN is transformed to a water soluble cyanide salt and cannot be stripped anymore. It would then be necessary to create acidic conditions via the addition of chemicals to protonate cyanide back to HCN before stripping.

The crude DNT containing mixture comprises at least 50 ppm of HCN, preferably at least 75 ppm of HCN. The crude DNT mixture comprises generally at most 500 ppm of HCN, preferably at most 200 ppm of HCN. A typical range is from 50 to 500 ppm, particularly from 75 to 200 ppm.

Since HCN is removed from the crude DNT phase before the first washing step, the wash water streams will not be contaminated with high levels of HCN or cyanide salts, and no further treatment of the waste water streams for the removal of HCN/cyanide salts will be necessary.

The distillation can be a simple flash evaporation under reduced pressure or a distillation under reflux using a distillation column having more than one theoretical plate. A stripping gas can be used in addition.

The distillation of the crude DNT containing mixture can be carried out in a distillation column having preferably up to 10 theoretical plates, more preferably up to 5 theoretical plates, in particular 2 to 4 theoretical plates. The distillation can be carried out without reflux in a flash evaporator.

In one embodiment of the present invention, the distillation of the crude DNT containing mixture is carried out in a flash evaporator. The flash evaporator is operated at a lower pressure than the phase separation unit in which the reaction mixture is separated into an aqueous phase and an organic phase containing mainly DNT. The pressure difference between the said phase separation unit and the flash evaporator is preferably at least 400 mbar. The distillation can be carried out in 2 or more consecutive flash evaporators which can be operated at the same pressure or different pressures. In one embodiment, the distillation is carried out in a multitude (at least 2) consecutive flash evaporators operated at successively decreasing pressures.

The distillation of the crude DNT containing mixture can be carried out under a pressure of from 10 mbar to 2 bar, preferably from 10 mbar to 500 mbar. In one preferred embodiment, a vacuum distillation is carried out under a pressure of from 10 mbar to 200 mbar.

In another preferred embodiment, a stripping operation, i.e., a separation by entrainment of the HCN with a stripping gas, is carried out. Preferably, the distillation in a column is combined with a stripping operation using a stripping gas. Distillation columns wherein distillation is carried out in the presence of a stripping gas are also termed stripping columns. Suitable stripping gases are nitrogen, air or steam.

In a preferred embodiment, air is used as the stripping gas. Air has a cost advantage over using nitrogen as stripping gas.

In another preferred embodiment, steam is used as a stripping gas. This is advantageous especially at low operating pressures of the stripping unit, as steam as stripping gas allows higher temperatures in the subsequent partial condensation unit, compared to the case where air or nitrogen is used as stripping gas.

The crude mixture comprising dinitrotoluene obtained from the distillation and/or stripping section is essentially free of HCN. "Essentially free of HCN" in the context of the present invention means that at least 70%, preferably at least 90% of the HCN present in the crude mixture before the distillation and/or stripping step has been carried out have been removed by the distillation and/or stripping step. In general, the crude DNT mixture comprises after the distillation and/or stripping step, but before the first washing step, generally at most 25 ppm of HCN, preferably at most 15 ppm of HCN.

The HCN content of the crude DNT containing mixture can be determined by a procedure consisting of steps (1)-(3):

(1) Extracting HCN and CN to an aqueous phase by intensively mixing the freshly drawn crude DNT sample with a mixture of demineralized water and an aqueous 2 wt.-% solution of $Na_2CO_3$. For the extraction, 0.5 g of aqueous 2 wt.-% $Na_2CO_3$ solution and 0.75 g of demineralized water per 1 g of crude DNT sample are added to the crude DNT sample.

(2) Separating the aqueous phase from the crude DNT phase.

(3) Analysing the aqueous phase using a headspace gaschromatography with mass selective detection (HS-GC/MS) according to reference method ME355.01 of the United States Enviromental Protection Agency.

The gaseous phase obtained from the top of the flash evaporator, stripping or distillation column may be partially condensed in order to recover nitric acid, sulfuric acid and organic compounds (mainly DNT) contained therein as condensate, while keeping most of the HCN in the gaseous phase. In general, at least 50% of the HCN are kept in the gaseous phase, preferably at least 70%, more preferably at least 80% of the HCN are kept in the gaseous phase. The partial condensation can likewise be carried out in an apparatus comprising only one single theoretical stage, such as a simple condenser, or in an apparatus containing more than one theoretical stage, e. g. in a multistep condenser, a distillation column or a stripping column. The partial condensation is carried out in general at a pressure of from 10 to 300 mbar and at a temperature of from 15 to 50° C. In one embodiment, the partial condensation is carried out in two steps, the first step being carried out at a pressure of from 20 to 50 mbar and a temperature of from 20 to 40° C., and the second step at a pressure of from 50 to 300 mbar and a temperature of from 30 to 50° C.

After the partial condensation of the heavy boilers, the partial condensate containing mainly DNT, nitric acid and sulfuric acid can be recycled to the reaction. The condensate can be at least in part recycled to one or more of the nitration steps (a), i. e., to the mononitration step leading to mononitrotoluene, to the dinitration step leading to dinitrotoluene, or to both nitration steps. The non-condensed, HCN rich gaseous stream can optionally undergo further (partial) condensation, can then be treated with chemicals, such as hydrogen peroxide, ozone or oxygen, or can be absorbed into an alkaline solution to remove HCN as cyanide salt, or can be sent to an incinerator.

The stream recovered at the base of the distillation or stripping vessel used for removing HCN, which stream comprises mainly DNT, sulfuric acid and organic byproducts, is then subjected to one or more washing steps such as to separate the DNT from the sulfuric acid and byproducts.

In one embodiment of the invention, a first step of washing with water is carried out to remove most of the sulfuric acid present. The obtained dilute sulfuric acid can advantageously be recycled into the process. For example, it may be reintroduced into the nitration process proper, preferably after having been subjected to a concentration step, by itself or in combination with another process stream such as, especially, the residual mononitration acid. Likewise, it may be recycled into the washing step itself.

In an optional second step, the stream of nitrated compounds is washed in the presence of an aqueous solution of an alkaline agent (basic washing). The purpose of such an operation is to convert the sulfuric acid and the byproducts, which are principally hydroxynitroaromatic compounds, into salts which are soluble in the aqueous phase.

This alkaline agent is advantageously selected from among alkali or alkaline earth metal hydroxides and carbonates.

Whether with regard to the first washing operation with water or with regard to the optional second operation in the presence of an alkaline agent, these operations may be carried out in one or more steps, preferably countercurrent steps, if the option involving multiple steps is selected.

The aromatic nitrated compounds which have undergone the basic washing step may then be washed again, but using water, to remove any trace amounts of the alkaline agent.

The present invention is illustrated by the following example.

EXAMPLE

A crude DNT stream (1) coming from the nitrator/phase separator (not shown) is fed to vacuum column C1 having 1 theoretical stage and operated at 30 mbara and 70° C. Liquid bottom withdrawal stream (3) from C1, mainly containing DNT and minor amounts of HCN, $H_2SO_4$ and $HNO_3$, is fed to the downstream washing part. Vaporous top withdrawal stream (2) from C1, mainly containing $HNO_3$, $NO_2/NO_x$ and most of the HCN contained in the crude DNT stream (1), is fed to partial condenser C2 operated at 30 mbara and 29° C. Liquid condensate stream (5) from C2, mainly containing $HNO_3$ and minor amounts of HCN, is recycled back to the nitrator (not shown). Non-condensed vapour stream (4) from C2, mainly containing HCN, NO and relatively low amounts of $HNO_3$ is fed to the vacuum pump P1 (P1 could be a jet pump, liquid ring pump, screw pump, etc), where it is compressed from 30 mbara to 200 mbara. The compressed stream (6) is fed to partial condenser C3 operated at 200 mbar and 40° C. Liquid condensate stream (8) from C3, mainly containing $HNO_3$ and minor amounts of HCN, is fed back to the nitrator (not shown) for $HNO_3$ recovery, Non-condensed vapour stream (7) from C3, mainly containing HCN, $HNO_3$ and $NO_x$, is fed to further off gas treatment. Off gas (7) contains around 86% HCN of the total HCN contained in the crude DNT stream (1), the rest about 14% HCN is recycled to the nitrator.

The results of the numerical simulation are given in Table 1, which gives the mass flow and the mass fraction for each of the components $H_2O$, $H_2SO_4$, $HNO_3$, HCN, $HNO_2$, $NO_2/NO_x$, DNT and cresol/organics for each of the process streams 1-8.

TABLE 1

| Stream | 1 | 2 | 3 | 4 | 5 | 6 | 7 | 8 |
|---|---|---|---|---|---|---|---|---|
| Temperature C. | 70 | 70 | 70 | 28.6 | 28.6 | 35 | 39.5 | 39.5 |
| Pressure bar | 1 | 0.03 | 0.03 | 0.03 | 0.03 | 0.2 | 0.2 | 0.2 |
| Total Mass Flow kg/hr | 1000 | 26.726 | 973.274 | 3.086 | 23.639 | 3.086 | 1.874 | 1.212 |
| Mass Flow kg/hr | | | | | | | | |
| H2O | 10 | 4.919 | 5.081 | 0.1280 | 4.791 | 0.128 | 0.005 | 0.123 |
| H2SO4 | 15 | 1 | 14 | 0 | 1 | 0 | 0 | 0 |
| HNO3 | 30 | 19.495 | 10.505 | 1.995 | 17.499 | 1.995 | 0.933 | 1.062 |
| HCN | 0.08 | 0.076 | 0.004 | 0.071 | 0.005 | 0.071 | 0.069 | 0.002 |
| HNO2 | 2 | 0 | 2 | 0 | 0 | 0 | 0 | 0 |
| NO2/NOx | 1 | 0.965 | 0.035 | 0.892 | 0.073 | 0.892 | 0.867 | 0.025 |
| DNT | 941.42 | 0.27 | 941.15 | 0 | 0.27 | 0 | 0 | 0 |
| CRESOL/organics | 0.5 | 0.001 | 0.499 | 0 | 0.001 | 0 | 0 | 0 |
| Mass Frac | | | | | | | | |
| H2O | 0.010 | 0.184 | 0.005 | 0.041 | 0.203 | 0.041 | 0.003 | 0.101 |
| H2SO4 | 0.015 | 0.037 | 0.014 | 0.06E+00 | 0.042 | 0.00 | 0.00 | 0.00 |
| HNO3 | 0.030 | 0.729 | 0.011 | 0.646 | 0.740 | 0.646 | 0.498 | 0.876 |

TABLE 1-continued

| Stream | 1 | 2 | 3 | 4 | 5 | 6 | 7 | 8 |
| --- | --- | --- | --- | --- | --- | --- | --- | --- |
| HCN | 8.00E−05 | 0.003 | 4.11E−06 | 0.023 | 2.12E−04 | 0.023 | 0.037 | 0.002 |
| HNO2 | 0.002 | 0.00 | 0.002 | 0.00 | 0.00 | 0.00 | 0.00 | 0.00 |
| NO2/NOx | 0.001 | 0.036 | 3.60E−05 | 0.289 | 0.003 | 0.289 | 0.463 | 0.021 |
| DNT | 0.941 | 0.010 | 0.967 | 0.00E+00 | 0.011 | 0.00 | 0.00 | 0.00 |
| CRESOL/organics | 0.001 | 3.74E−05 | 0.001 | 0.00E+00 | 4.23E−05 | 0.00 | 0.00 | 0.00 |

The invention claimed is:

1. A process for the preparation of dinitrotoluene which comprises
    (a) nitrating toluene with a nitrating acid, wherein said nitrating acid is a mixture of nitric acid and sulfuric acid, in one or more nitration steps, and separating the nitrating acid from the process stream thus formed, wherein a crude mixture comprising dinitrotoluene and a fraction of said nitrating acid dissolved therein is obtained, said crude mixture further comprising at least 50 ppm of HCN, and
    (b) washing the crude dinitrotoluene containing mixture in one or more washing steps,
    wherein, before the first washing step is carried out, the crude mixture is distilled and/or stripped in a flash evaporator, stripping or distillation column to remove HCN therefrom, wherein a crude dinitrotoluene containing mixture which is essentially free of HCN is obtained, and the gaseous phase obtained from the top of the flash evaporator, stripping or distillation column is partially condensed in order to recover a condensate containing nitric acid, sulfuric acid and dinitrotoluene while keeping as least 50% of the HCN in the gaseous phase.

2. The process of claim 1, wherein the crude dinitrotoluene containing mixture is distilled in a column having up to 10 theoretical plates.

3. The process of claim 2, wherein the crude dinitrotoluene containing mixture is distilled in a column having 2 to 4 theoretical plates.

4. The process of claim 1, wherein the crude dinitrotoluene containing mixture is distilled in a flash evaporator.

5. The process according to claim 1, wherein the distillation is carried out as a vacuum distillation at a pressure of from 10 to 200 mbar.

6. The process according to claim 1, wherein the distillation is combined with a stripping operation using a stripping gas.

7. The process according to claim 6, wherein the stripping operation is carried out using air or nitrogen as a stripping gas.

8. The process according to claim 1, wherein the gaseous phase obtained in the distillation and/or stripping is partially condensed in a multistep condenser.

9. The process of claim 8, wherein the liquid condensate phase comprising dinitrotoluene, nitric acid and sulfuric acid is at least in part recycled to one or more of the nitration steps (a).

10. The process of claim 1, wherein at least 90% of the HCN present in the crude dinitrotoluene containing mixture are removed by the distillation and/or stripping before the first washing step.

11. The process of claim 1, wherein the crude dinitrololuene containing mixture after the distillation and/or stripping, but before the first washing step has been carried out, contains at most 15 ppm of HCN.

* * * * *